United States Patent [19]
Bolea et al.

[11] Patent Number: 6,025,189
[45] Date of Patent: *Feb. 15, 2000

[54] APPARATUS FOR READING A PLURALITY OF BIOLOGICAL INDICATORS

[75] Inventors: Phillip A. Bolea, White Bear Lake; Thomas T. Rosenlund, Stillwater, both of Minn.

[73] Assignee: 3M Innovative Properties Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/967,747

[22] Filed: Nov. 10, 1997

Related U.S. Application Data

[63] Continuation-in-part of application No. 08/866,894, May 30, 1997, Pat. No. 5,863,790, and application No. 08/856,104, May 14, 1997, abandoned.

[51] Int. Cl.⁷ ................................................ C12M 1/34
[52] U.S. Cl. ............................ 435/287.4; 435/287.3; 435/288.7; 435/303.1; 435/31
[58] Field of Search ................. 435/287.1, 287.3, 435/287.4, 288.1, 288.7, 303.1, 304.1, 809, 808, 31, 34; 422/82.08, 63–65; 436/172; 250/328; 356/246

[56] References Cited

U.S. PATENT DOCUMENTS

| | | | |
|---|---|---|---|
| 3,535,208 | 10/1970 | Sasaki et al. | 435/809 |
| 3,542,515 | 11/1970 | Scott | 23/230 |
| 3,701,601 | 10/1972 | Plumpe, Jr. et al. | 356/96 |
| 3,776,817 | 12/1973 | Van Der Pfordten | 195/103.5 R |
| 3,801,467 | 4/1974 | Nobe et al. | 435/809 |
| 3,928,140 | 12/1975 | Wyatt et al. | 195/103.5 R |
| 3,983,006 | 9/1976 | Acker et al. | 195/103.5 R |
| 3,999,948 | 12/1976 | Deindoerfer et al. | 23/230 B |
| 4,043,756 | 8/1977 | Sommervold | 23/230 R |
| 4,055,752 | 10/1977 | Kappe et al. | 364/551 |
| 4,056,361 | 11/1977 | Peters et al. | 23/259 |

(List continued on next page.)

FOREIGN PATENT DOCUMENTS

| | | |
|---|---|---|
| 0 607 941 A2 | 7/1994 | European Pat. Off. . |
| 94/09698 | 9/1994 | WIPO . |
| WO 95/08639 | 3/1995 | WIPO . |
| WO 95/21382 | 8/1995 | WIPO . |

OTHER PUBLICATIONS

"Fluorimetric Detection of a *Bacillus stearothermophilus* Spore–Bound Enzyme, α–D–Glucosidase, for Rapid Indication of Flash Sterilization Failure", Applied and Environmental Microbiology, vol. 58, No. 2, Feb. 1992, pp. 717–719.

"Fluorometric Procedure for Measuring the Activity of Dehydrogenases", Analytical Chemistry, vol. 37, No. 10, Sep. 1965, pp. 1219–1221.

"New Direct Fluorometric Method for Measuring Dehydrogenase Activity", Analytical Chemistry, vol. 36, No. 13, Dec. 1964, pp. 2497–2498.

(List continued on next page.)

*Primary Examiner*—William H. Beisner
*Attorney, Agent, or Firm*—Gary L. Griswold; Eloise J. Maki; Jeffrey J. Hohenshell

[57] ABSTRACT

An apparatus reads a plurality of biological indicators (BIs) to determine efficacy of a plurality of sterilization cycles. Each BI exhibits fluorescence in response to biological activity indicative of bacterial growth in the BI. A plurality of BI holders are each configured to receive one of the BIs. A carriage is controllably movable relative to the plurality of BI holders to positions proximate each of the BI holders. A fluorescence sensor is mounted on the carriage and is positioned to sense fluorescence exhibited by the BI contained in the BI vessel in the selected BI holder. A controller is coupled to the fluorescence sensor to receive a fluorescence signal and to provide an output signal indicative of the fluorescence sensed.

30 Claims, 9 Drawing Sheets

U.S. PATENT DOCUMENTS

| | | | |
|---|---|---|---|
| 4,059,405 | 11/1977 | Sodickson et al. | 422/82.08 |
| 4,189,236 | 2/1980 | Hogg et al. | 356/317 |
| 4,200,802 | 4/1980 | Salzman et al. | 250/461 B |
| 4,240,751 | 12/1980 | Linnecke et al. | 356/409 |
| 4,254,223 | 3/1981 | Schuurs et al. | 435/296 |
| 4,293,643 | 10/1981 | Ohtake et al. | 435/39 |
| 4,528,268 | 7/1985 | Andersen et al. | 435/31 |
| 4,579,823 | 4/1986 | Ryder | 435/296 |
| 4,626,684 | 12/1986 | Landa | 250/328 |
| 4,657,870 | 4/1987 | Ryder et al. | 435/311 |
| 4,720,463 | 1/1988 | Farber et al. | 435/809 |
| 4,849,172 | 7/1989 | Yafuso et al. | 422/82.08 |
| 4,857,273 | 8/1989 | Stewart | 422/68 |
| 4,936,682 | 6/1990 | Hoyt | 356/414 |
| 4,940,332 | 7/1990 | Miwa et al. | 356/417 |
| 5,030,832 | 7/1991 | Williams et al. | 250/458.1 |
| 5,035,861 | 7/1991 | Grandone | 422/64 |
| 5,063,297 | 11/1991 | Hardenbrock et al. | 250/458 |
| 5,064,619 | 11/1991 | Finlan | 422/82.05 |
| 5,073,488 | 12/1991 | Matner et al. | 435/31 |
| 5,156,976 | 10/1992 | Slovacek et al. | 436/164 |
| 5,164,301 | 11/1992 | Thompson et al. | 435/29 |
| 5,164,597 | 11/1992 | Lodder | 250/341 |
| 5,164,796 | 11/1992 | Diguiseppi et al. | 356/445 |
| 5,167,923 | 12/1992 | Van Iperen | 422/58 |
| 5,173,434 | 12/1992 | Morris et al. | 436/172 |
| 5,223,401 | 6/1993 | Foltz et al. | 435/18 |
| 5,240,857 | 8/1993 | Lahetkangas | 435/303.1 |
| 5,244,637 | 9/1993 | Pratellesi et al. | 422/102 |
| 5,252,484 | 10/1993 | Matner et al. | 435/288 |
| 5,324,635 | 6/1994 | Kawase et al. | 435/7.94 |
| 5,334,841 | 8/1994 | Graessle et al. | 250/458.1 |
| 5,340,715 | 8/1994 | Slovacek et al. | 435/6 |
| 5,340,747 | 8/1994 | Eden | 436/172 |
| 5,372,784 | 12/1994 | Morris et al. | 422/82.08 |
| 5,374,395 | 12/1994 | Robinson et al. | 422/64 |
| 5,380,493 | 1/1995 | Chavez et al. | 422/104 |
| 5,418,167 | 5/1995 | Matner et al. | 435/288 |
| 5,432,061 | 7/1995 | Berndt et al. | 435/34 |
| 5,456,883 | 10/1995 | Burkovich et al. | 422/64 |
| 5,474,910 | 12/1995 | Alfano | 435/34 |
| 5,480,804 | 1/1996 | Niwa et al. | 435/286.1 |
| 5,486,459 | 1/1996 | Burnham et al. | 435/31 |
| 5,498,543 | 3/1996 | Berndt | 435/286.1 |
| 5,516,692 | 5/1996 | Berndt | 435/286.7 |
| 5,518,923 | 5/1996 | Berndt et al. | 435/287.3 |
| 5,525,466 | 6/1996 | Slovacek et al. | 435/6 |
| 5,538,850 | 7/1996 | King et al. | 435/6 |
| 5,545,561 | 8/1996 | Lleonart Aliberas | 439/287.3 |
| 5,554,340 | 9/1996 | Lackie | 422/82.08 |
| 5,559,002 | 9/1996 | Uzan et al. | 435/7.9 |
| 5,565,634 | 10/1996 | Graessle et al. | 73/865.9 |
| 5,573,950 | 11/1996 | Graessle et al. | 435/287.3 |
| 5,580,784 | 12/1996 | Berndt | 435/288.7 |
| 5,591,644 | 1/1997 | Karmen | 436/53 |
| 5,593,854 | 1/1997 | Berndt | 435/31 |
| 5,595,709 | 1/1997 | Berndt | 422/82.06 |
| 5,779,983 | 7/1998 | Dufresne et al. | 422/102 |
| 5,830,683 | 11/1998 | Hendricks et al. | 435/31 |
| 5,863,790 | 1/1999 | Bolea | 435/287 |

OTHER PUBLICATIONS

"3M Attest Rapid Readout Biological Monitoring System for 250°F/121°C C Gravity, 270°F/132°C Vacuum Assisted Sterilizers", 3M Health Care, 1995.

"Attest Rapid Readout Biological Monitoring System for 270°F/132°C Gravity Displacement Steam (flash) Sterilizers", 3M Health Care, 1993.

"Attest Rapid Readout Biological Monitoring System for 270°F/132°C Gravity Displacement Steam Sterilization", 3M Health Care, Sep. 1990.

"Attest Biological Monitoring System", 3M Health Care (brochure—admitted prior art) No Date Provided.

APPARATUS FOR READING A PLURALITY OF BIOLOGICAL INDICATORS

REFERENCE TO CO-PENDING APPLICATIONS

This application is a continuation-in-part of U.S. patent application No. 08/866,894, filed May 30, 1997 entitled, "Biological Sterility Indicator" (now U.S. Pat. No. 5,863, 790); and this application is also a continuation-in-part of U.S. patent application No. 08/856,104, filed May 14, 1997, entitled "System For Measuring The Efficacy of a Sterilization Cycle".

BACKGROUND OF THE INVENTION

The present invention relates to a system for determining the efficacy of a sterilization cycle. More specifically, the present invention relates to a system for reading fluorescence from a biological sterility indicator in order to determine the efficacy of the sterilization cycle.

The sterilization of equipment and devices is critical in some industries. For example, hospitals and other medical institutions must commonly and frequently sterilize equipment and devices used in treating patients. The particular type of sterilization cycle used to sterilize such equipment can vary based on the particular equipment or devices being sterilized and based on the particular preference of the entity performing the sterilization cycle. However, all such sterilization cycles or processes are typically designed to kill living organisms which might otherwise contaminate the equipment or devices being sterilized.

Various sterilization cycles use different methods or techniques for sterilization. For instance, such sterilization cycles may include the administration of steam, dry heat, chemicals, or radiation, to the equipment or devices being sterilized. Steam sterilization is typically efficacious when the equipment being sterilized are exposed to steam having a temperature in a range of 121–132° C. The equipment being sterilized are preferably exposed to the steam sterilization for approximately three minutes at 132° C., and ranging to 30 minutes at 121° C. One form of chemical sterilization involves exposing the devices to be sterilized to ethylene oxide gas. The devices being sterilized are exposed to the ethylene oxide gas for approximately one hour at 65° C. to approximately four hours at 30° C. Dry heat sterilization typically involves exposing the devices being sterilized to temperatures in a range of approximately 180° C., or higher, for at least two hours.

In many environments, the efficacy of the sterilization cycle is critical. Therefore, sterility indicators are used to determine the efficacy of the sterilization cycle.

The sterility indicators have taken a number of forms in the past. For example, biological indicators and chemical indicators are well known in the art. In conventional biological indicators, a test organism which is many times more resistent to the sterilization process than most organisms which would be present by natural contamination, is coated on a carrier and placed in a sterilizer along with the articles to be sterilized. Thus, the sterility indicator is exposed to the same sterilization cycle as the devices being sterilized. After completion of the sterilization cycle, the carrier is incubated in nutrient medium to determine whether any of the test organisms survived the sterilization procedure. Growth of a detectable number of organisms normally takes at least approximately 24 hours.

The sterility indicator is then examined to determine whether such growth has taken place. If so, such growth indicates that the sterilization cycle has not been efficacious, and it can be assumed that the devices which were subject to the sterilization cycle are not sterile.

Commercially available chemical indicators utilize chemicals which indicate sterility by color changes, or change from a solid to liquid state. One advantage to such chemical indicators is that the results are known by the end of the sterilization cycle. However, the results only indicate, for example, that a particular temperature has been reached for a certain period of time, or that ethylene oxide gas was present, during the sterilization cycle. The chemical indicators do not indicate whether conditions necessary for eliminating the organisms of interest have been achieved. Thus, the industry has shown a preference for biological indicators which use living organisms.

Another type of prior biological indicator is disclosed in Matner et al. (U.S. Pat. No. 5,418,167). Matner et al. describes a biological indicator in which a flexible polypropolene vial contains a spore strip which has a viable population of Bacillus Stearothermophilus spores. The vial also contains a growth medium which is a modified tryptic soy broth contained in a crushable glass ampule. The presence of a spore-associated enzyme, alpha-glucosidase, indicates spore growth in the biological indicator. The presence of alpha-glucosidase is measured by using a non-fluorescent substrate, 4-methylumbelliferyl-alpha-D-glucoside. The non-fluorescent substrate is converted by the active spore-associated enzyme to a fluorescent product.

If the sterilization cycle is not efficacious, both the spore and the enzyme remain active. The enzyme converts the substrate to a fluorescent product. Therefore, the fluorescence in the vial is detected, after an incubation period, to determine the efficacy of the sterilization cycle.

While Matner et al. represents a significant advancement in the art, the system for reading the biological indicator set out in Matner et al. suffers from a number of disadvantages. Matner et al.'s system is configured to read only one biological indicator at a time. Therefore, the operator places the biological indicator (BI) in a single heater, which is set to heat the biological indicator to one set temperature. The operator then sets a timer. When the timer goes off, the operator removes the biological indicator from the incubator (or heater) and places the biological indicator in the single reading cell taught by Matner, et al. The fluorescence reading is taken for the biological indicator, and an indication is provided to the operator as to whether spore growth activity is exhibited in the biological indicator (and, hence, whether the sterilization cycle to which the biological indicator has been exposed was efficacious).

Processing BIs in this way leads to a cumbersome system for tracking multiple biological indicators. First, since the system only provides a single incubator which heats to a single temperature, a separate biological indicator reading apparatus must be used in order to read different types of biological indicators (i.e., those which must be incubated at different temperatures for different time periods) Further, the user must independably chart the time when each BI was placed in the incubator, track the duration that each BI is incubated, and record the results of the reading step for each BI so as to chart the efficaciousness of each associated sterilization cycle. Also, in order to take a fluorescence reading from even a single BI, the operator must handle that BI several times. The operator must place the BI in the incubator and remove the BI when reading is desired. Then, if additional incubation or readings are desired, the operator must again place the BI in the incubator and again remove the BI for subsequent reading.

In addition, in the Matner, et al. system, the fluorescence sensor is configured to sense fluorescence emitted from one small spot on the biological indicator vessel. Thus, fluorescent activity is sensed only from a portion of the BI and not from the entire external periphery of the BI. A signal is generated based on this small amount of sensed fluorescence. This yields a sensor signal with a relatively low amplitude which must be greatly amplified in order to obtain a signal with a desirably high amplitude which can be utilized in further processing. However, the necessary amplification introduces a significant source of error in the sensor signal and also reduces the signal-to-noise ratio corresponding to the fluorescence signal.

SUMMARY OF THE INVENTION

An apparatus reads a plurality of biological indicators contained in a biological indicator vessel (the indicator and the vessel being collectively referred to as a BI) to determine efficacy of a plurality of sterilization cycles. Each BI exhibits fluorescence in response to biological activity indicative of bacterial growth in the vessel. A plurality of BI holders are each configured to receive one of the BIs. A carriage is controllably movable relative to the plurality of BI holders to positions proximate each of the BI holders. A radiation emitter is mounted on the carriage and is positioned to impinge radiation on a BI received in a selected BI holder. A fluorescence sensor is also mounted on the carriage and is positioned to sense fluorescence exhibited by the BI in the selected BI holder in response to the radiation. A controller is coupled to the fluorescence sensor to receive a fluorescence signal and to provide an output signal indicative of the fluorescence sensed. The controller is configured to control the position of the carriage to intermittently position the carriage proximate each of the BI holders then holding a BI. A memory is coupled to the controller and is configured to receive and store data indicative of the fluorescence of each BI based on the fluorescence signals received by the controller.

In one preferred embodiment, a second controller is provided on the carriage which processes the signal provided by the fluorescence sensor and which provides a fluorescence signal to the first controller.

In another preferred embodiment, a plurality of independently controllable heaters are provided so that different types of biological indicators can be incubated and read by a single system.

In yet another preferred embodiment, an integration cavity is provided around each BI in the incubator. The integration cavity collects fluorescence from a large portion of an exterior portion of the BI and directs the fluorescence toward the fluorescence sensor. This tends to compensate for non-uniformities. Also, a higher amplitude and more robust sensor signal is provided, which requires less amplification.

DETAILED DESCRIPTION OF THE PREFERRED EMBODIMENTS

Figure 1:
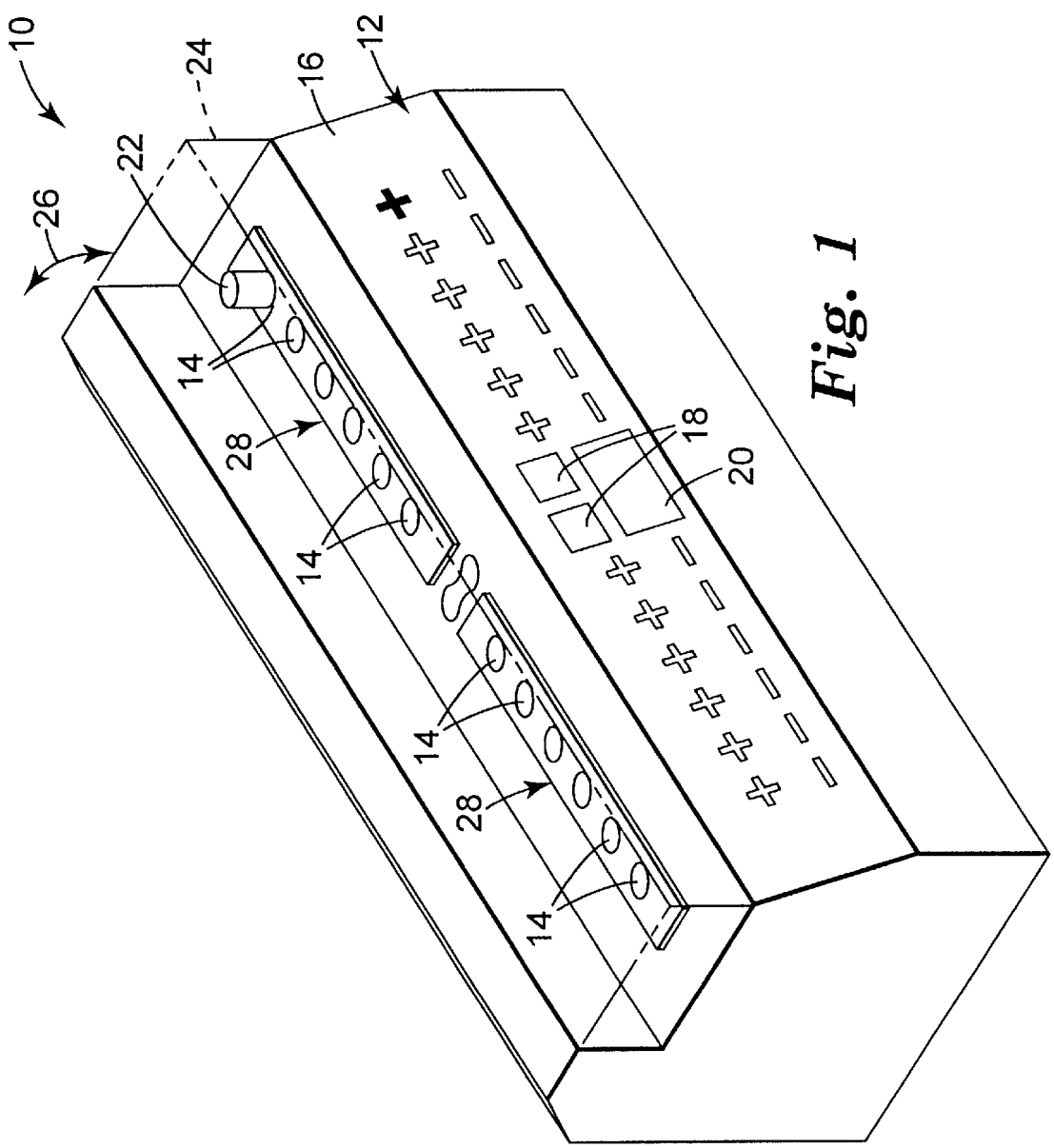
FIG. 1 is a perspective view of a biological indicator apparatus in accordance with one embodiment of the present invention.

FIG. 1 is a perspective view of one embodiment of a biological indicator (BI) reading apparatus 10. BI reading apparatus 10 includes housing 12, which provides a plurality of DI receiving wells 14. Each receiving well 14 has an associated display on display panel 16. In addition, operator interaction is accomplished with optional scroll buttons 18 and operator display 20. FIG. 1 shows a BI 22 residing in one of the BI receiving wells 14. FIG. 1 also illustrates cover 24, which is pivotable generally along an arc 26 to alternately expose and cover BI receiving wells 14.

In the embodiment shown in FIG. 1, BI receiving wells 14 are arranged in two groups. The first group is associated with first incubator zone 28, and a second group is associated with a second incubator zone 30. As will be described with greater detail later in the application, first incubator zone 28 is associated with a first heater that heats the corresponding BI receiving wells 14 to a first temperature. Second incubator zone 30 is associated with a second heater that heats corresponding BI receiving wells 14 to a second temperature. In this way, multiple types of biological indicators can be simultaneously accommodated. In addition, and as will be described in greater detail later in the application, substantially all of the biological indicator reading circuitry is contained within housing 10.

In the preferred embodiment, the biological indicator substance and corresponding vessels (collectively referred to as BIs) 22 are biological sterility indicators commercially available from the Minnesota Mining and Manufacturing Company of Saint Paul, Minn., under the tradename 3M ATTEST, models 1291 or 1292. BI 22 includes a cap, a vial, and various contents (not shown). BI 22 evidences the presence of a viable microorganism (such as spores) by the production of fluorescence within the vial after incubation in one of incubator zones 28 and 30. This is preferably accomplished by using a non-fluorescent substrate (such as 4-methylumbelliferyl-alpha-D-glucoside) in the vial and converting that non-fluorescent substrate to a fluorescent product by spore-associated enzyme activity. The spore-associated enzyme is preferably alpha-D-glucoside, which is one of the enzymes involved in the growth of the spore within the vial.

In operation, the operator first retrieves a biological indicator 22, which must be incubated and read. The operator then cracks an ampule (not shown) in the BI 22 and places the BI 22 into a suitable BI receiving well 14. The operator can then either program the incubator zone 28 or 30 using scroll buttons 18 and observing display 20, or the operator can configure incubator zones 28 and 30 prior to placing BI 22 into BI receiving well 14.

In any case, once the incubator zone is configured, the operator simply closes cover 24 and waits for either a positive or a negative indication to be displayed on display panel 16 for the associated biological indicator contained in the BI 22. Since substantially all of the fluorescence reading circuitry is contained in housing 12 and is configured to read BI 22 while it resides in BI receiving well 14, and since BI 22 is incubated while it resides in BI receiving well 14, the number of steps required by the operator and the cumbersome nature of prior BI reading apparatus are substantially alleviated.

Figure 2:
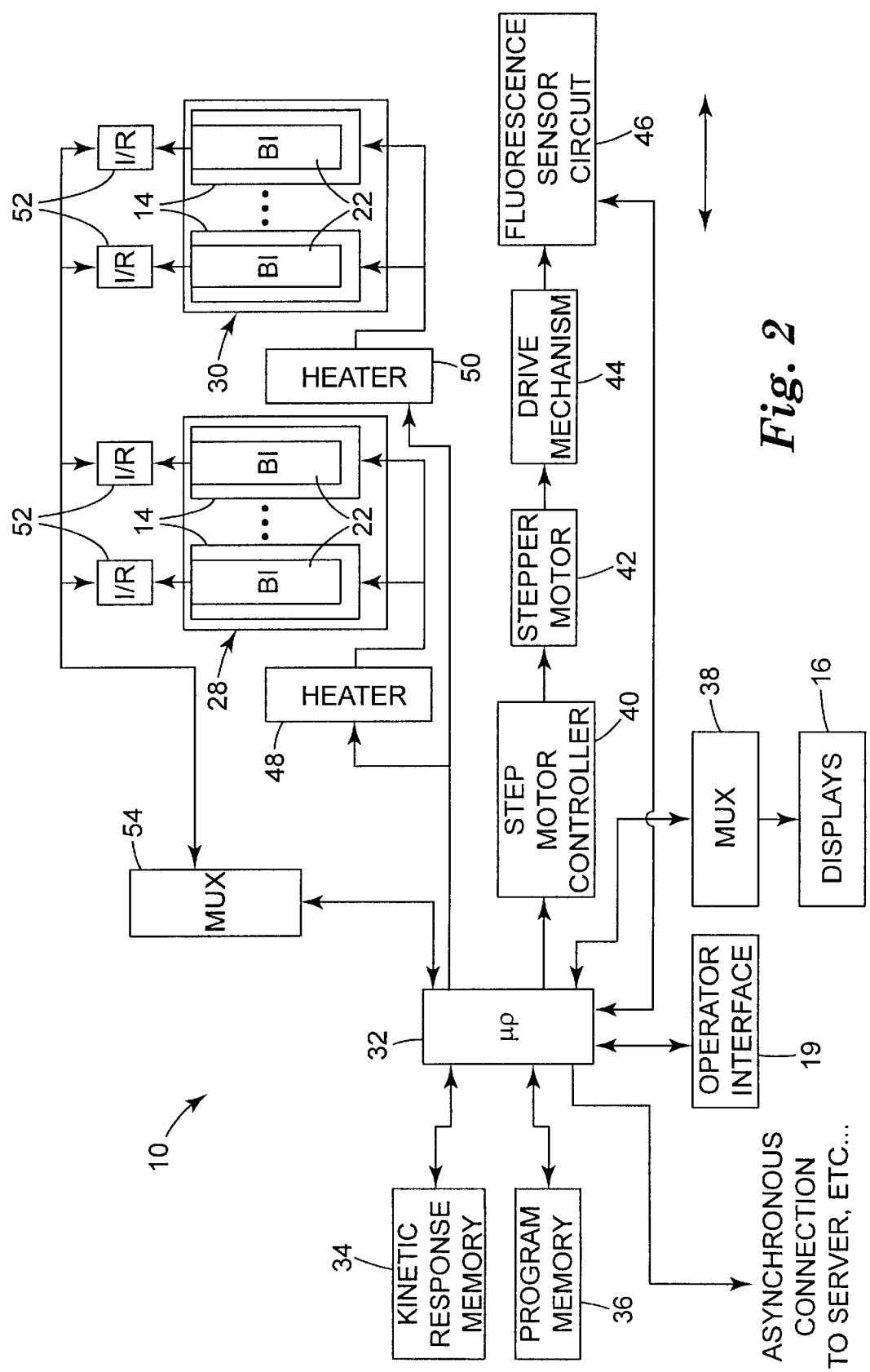
FIG. 2 is a block diagram of a portion of the biological indicator apparatus shown in FIG. 1.

FIG. 2 illustrates a more detailed block diagram of biological indicator reading apparatus 10, as shown in FIG. 1. Similar items to those shown in FIG. 1 are similarly numbered. BI reading apparatus 10 includes microprocessor 32 with associated kinetic response memory 34 and programmable memory 36. BI reading apparatus 10 also includes display 16, multiplexer 38, operator input and displays 18, 20 (collectively referred to as operator interface 19), step motor controller 40, stepper motor 42, drive mechanism 44, fluorescence sensor circuit 46, first heater 48, second heater 50, a plurality of BI presence sensors 52, and multiplexer 54. Also, in a preferred embodiment, microprocessor 32 is configured to be asynchronously coupled for communication with other systems or servers.

In a preferred embodiment, microprocessor 32 is a suitable microprocessor or microcontroller programmed to control desired operations. Microprocessor 32 preferably includes either an integrated timing device or a separate timer circuit for accomplishing timing in the circuitry of BI reading apparatus 10. Program memory 36 is preferably a read only memory, either integrated with microprocessor 32 or associated therewith. Memory 34 is preferably random access memory (RAM) or other suitable memory for storing data that is received by microprocessor 32 and reflects the kinetic behavior response of BIs during the fluorescence reading operations.

Stepper motor 42 and step motor controller 40 are preferably conventional and commercially available items. Drive mechanism 44 is preferably a linear drive mechanism (as discussed in greater detail with respect to FIG. 4) or is a rotary drive mechanism (as discussed in greater detail with respect to FIGS. 9 and 10).

Heaters 48 and 50 are preferably programmable heaters which can be configured to heat to various temperatures. Also, heaters 48 and 50 preferably have an associated thermistor for sensing temperature and providing a feedback signal to microprocessor 32, such that closed loop control of heaters 48 and 50 is accomplished. In one preferred embodiment, heater 48 is configured to heat to 60° C., while heater 50 is configured to heat to 37° C. Heaters 48 and 50 are coupled by a highly thermally conductive material to BI receiving wells 14. Thus, heater 48 heats an associated group of BI receiving wells 14 to approximately 60° C., while heater 50 heats an associated group of BI receiving wells 14 to approximately 37° C.

BI presence sensors 52 are preferably infrared detectors. In one preferred embodiment, a BI presence sensor 52 is associated with each BI receiving well 14. BI presence sensors 52 are configured to detect the presence of a BI 22 in an associated BI receiving well 14. BI presence sensors 52 are also coupled, through multiplexer circuit 54, to microprocessor 32.

Fluorescence sensor circuit 46, in one preferred embodiment (and as will be described in greater detail with respect to FIG. 3) is provided with a flash mechanism and a fluorescence sensor. Fluorescence sensor circuit 46 is mounted on a carriage assembly, which will also be described in greater detail later in the application, for movement relative to BI receiving wells 14. In the preferred embodiment, fluorescence sensor circuit 46 is movable among positions proximate each BI receiving well 14 to take fluorescence readings from a BI 22 received in the BI receiving wells 14.

A BI 22 is first placed in a sterilizer along with the other devices or equipment to be sterilized. Then, the sterilization cycle is performed. The sterilization cycle may typically include steam sterilization, dry heat sterilization, or chemical or radiation sterilization techniques. Different time frames, temperature regimes and sterilization cycles require the use of different types of BIs, as is known. In any case, the BI 22 is subjected to the sterilization cycle.

The operator then, in one preferred embodiment, inputs into reading apparatus 10 (preferably through operator interface 19) the particular type of BI being used as BI 22. This accomplishes a number of things. First, the particular type of BI being used indicates microprocessor 32 the correct set point for the heater 48 or 50 associated with the reading well 14 into which the BI 22 will be placed. For instance, one type of BI may require incubation at approximately 60° C. while another type may require incubation at approximately 37° C. Of course, the heaters could also simply be pre-configured by the operator. In any case, microprocessor 32 preferably controls the heaters to desired set points with closed loop control.

In addition, based on the type of BI being used, microprocessor 32 retrieves from memory corresponding fluorescent kinetic behavior information for use in providing the efficacy output. The kinetic information is preferably indicative of the fluorescent behavior of the particular BI under circumstances in which the sterilization cycle to which it was exposed has been efficacious and non-efficacious.

BI 22 is then conditioned for spore growth. In the embodiment in which BI 22 is implemented as the 3M ATTEST model 1291 BI, the glass ampule containing a growth medium is crushed and its contents are applied to a dry strip containing the spores. BI 22 is then ready for incubation and is placed in a well 14.

Microprocessor 32 periodically takes readings from BI presence sensors 52 through multiplexer 54. If none of the BI presence sensors 52 have provided a signal indicating that a BI is present in a well 14, microprocessor 32 simply continues to intermittently read from sensors 52. If the operator has placed a BI 22 in a well 14, but still no signal is received from sensors 52, the operator may not have seated BI 22 all the way into BI receiving well 14. That being the case, the biological sterility indicator contained in BI 22 may not receive the full heat from the corresponding heater 48 or 50 and, thus, may not receive adequate incubation. Further, BI 22 (if it is not seated fully within BI receiving well 14) may not be in a proper position for an accurate fluorescence reading to be taken. Therefore, the operator, upon being prompted by microprocessor 32 that no BIs 22 are fully seated in BI receiving wells 14, can take corrective measures to fully seat BI 22 in BI receiving well 14.

Upon receiving a signal from one of BI presence sensors 52 that a BI 22 is seated within BI receiving well 14, microprocessor 32 controls the circuit to take a plurality of fluorescence readings from that BI 22. Microprocessor 32 first provides an output to step motor controller 40, which causes stepper motor 42 to manipulate drive mechanism 44 to position fluorescence sensor circuit 46 at a position proximate the BI receiving well 14 which is populated with BI 22. Microprocessor 32 then controls fluorescence sensor circuit 46 to take a plurality of fluorescence readings from BI 22. Results of the fluorescence reading are provided to microprocessor 32 and are stored by microprocessor 32 in kinetic response memory 34.

In a preferred embodiment, kinetic response memory 34 is divided into blocks, one block being associated with each BI 32 then being processed. That block of kinetic response memory then contains the data indicative of a plurality of fluorescence readings, over time, for a given BI 22. That kinetic data is processed by microprocessor 32 in order to provide an output to display panel 16, indicating whether the sterilization cycle associated with that particular BI 22 has been efficacious.

The particular method by which the readings are taken can be implemented in a number of ways described in more detail with respect to U.S. Patent application Ser. No. 08/856,104, entitled "SYSTEM FOR MEASURING THE EFFICACY OF A STERILIZATION CYCLE", filed on May 14, 1997, assigned to the same assignee as the present application and hereby fully incorporated by reference. Briefly, the operator, upon placing BI 22 in receiving well 14, indicates through operator interface 19 the type of BI being used. Microprocessor 32 then identifies in either program memory 36 or kinetic response memory 34 corresponding kinetic behavior information for use in providing the efficacy output. The kinetic behavior information is preferably information which is indicative of fluorescence readings that correspond to efficacious and non-efficacious sterilization cycles for that particular type of BI.

A first florescence reading is then taken at approximately time 0 (prior to any significant incubation) but after the glass ampule has been broken (i.e., after the BI has been wetted out). This fluorescence reading is indicative of the autoflourescent behavior of the particular BI 22, at that time, for which the reading is being taken. In addition, unless the BI 22 was contaminated prior to the sterilization cycle, the first fluorescence reading does not include fluorescence attributable to any significant spore growth.

Microprocessor 32 then compares the first fluorescence reading to a predetermined threshold level stored in kinetic response memory 34. If the first reading exceeds the threshold level, this indicates that the particular BI 22 for which the first reading is being taken has been contaminated prior to the sterilization cycle, such as at the manufacturer of that particular BI 22. In other words, if BI 22 is contaminated prior to the sterilization cycle, significant spore growth or bacterial activity will have already taken place in that BI 22 prior to any incubation. Thus, the initial first florescence reading will reflect quite a high degree of florescence, much higher than the autoflourescent behavior expected from an uncontaminated BI. Therefore, if the microprocessor 32 determines that the first florescence reading from BI 22 exceeds the threshold, microprocessor 32 provides an output on operator interface 19 indicating that the particular BI 22 for which the reading was taken has been contaminated and the efficacy of that particular sterilization cycle cannot be determined.

If BI 22 has not been contaminated, microprocessor 32 preferably controls fluorescence sensor circuit 46 to take a number of readings to look for a local minima in the kinetic response information associated with that particular type of BI. The florescence reading taken at that time corresponds to a baseline florescence reading for the particular BI 22 being read.

The baseline florescence reading is taken and stored by microprocessor 32 in the corresponding portion of kinetic response memory 34 associated with that particular BI 22. The initial or baseline florescence reading is indicative of the autoflourescent behavior of the particular BI 22 for which the reading is being taken. In addition, unless BI 22 is contaminated prior to the sterilization cycle, the baseline or threshold reading will not include florescence attributable to any significant spore growth.

After the baseline reading is obtained, microprocessor 32 waits for a designated time out. The length of the time out will correspond to the particular BI type being used, and how fast spore growth activity is expected to occur. Such a time out may be, for example, one to three minutes, or more, as desired.

During the desired time out, microprocessor 32 can attend to other desired activities. For instance, microprocessor 32 may position fluorescence sensor circuit 46 proximate other BI receiving wells 14 to take florescence readings from other BIs 22. Since the operator of system 10 can place a BI 22 in a reading well at any time, and asynchronously with other BIs 22, such BIs 22 can be asynchronously incubated and processed by microprocessor 32. Therefore, during the time out period, microprocessor 32 preferably performs other operations associated with processing of other BIs 22.

After the desired time out, another florescence reading is taken from the particular BI 22. After this secondary florescence reading is taken from BI 22, microprocessor 32 compares that florescence reading with the baseline florescence taken for that particular BI 22 (and which has been stored in kinetic response memory 34). If microprocessor 32 determines that the second florescence reading exceeds the baseline florescence reading by a statistically significant amount, that means that a statistically significant amount of biological activity (spore growth) has occurred in BI 22 during the incubation cycle. Thus, the sterilization cycle has not been efficacious. Microprocessor 32 therefore provides an output to display panel 16 indicating that the sterilization cycle has not been efficacious.

If the spore growth rate determined for the particular BI 22 under analysis does not exceed the baseline florescence reading by a statistically significant amount, then microprocessor 32 determines whether additional incubation time is required. The biological indicator may be incubated for anywere between 5 and 15 minutes, or more. However, it has been observed that using the present system of reading BI 22, the efficacy of the sterilization cycle can often be determined for biological indicators after only five minutes, for the vast majority of biological indicators in less than 10 minutes, and for substantially all biological indicators of this type in less than 15 minutes. The operator simply needs to program microprocessor 32 to incubate the biological indicator for sufficient time that an adequate confidence level is achieved which indicates that there is no spore growth activity, and that there will be none, in the particular BI 22 under analysis. This time is preferably determined by empirical characterization studies of the various types of BIs to be analyzed.

Once microprocessor 32 determines that the secondary florescence reading has not exceeded the baseline florescence reading by a statistically significant amount, and once microprocessor 32 determines that no additional incubation time is required, microprocessor 32 provides an output to the operator via multiplexer 38 and display panel 16 indicating that the sterilization cycle has been efficacious.

Figure 3:
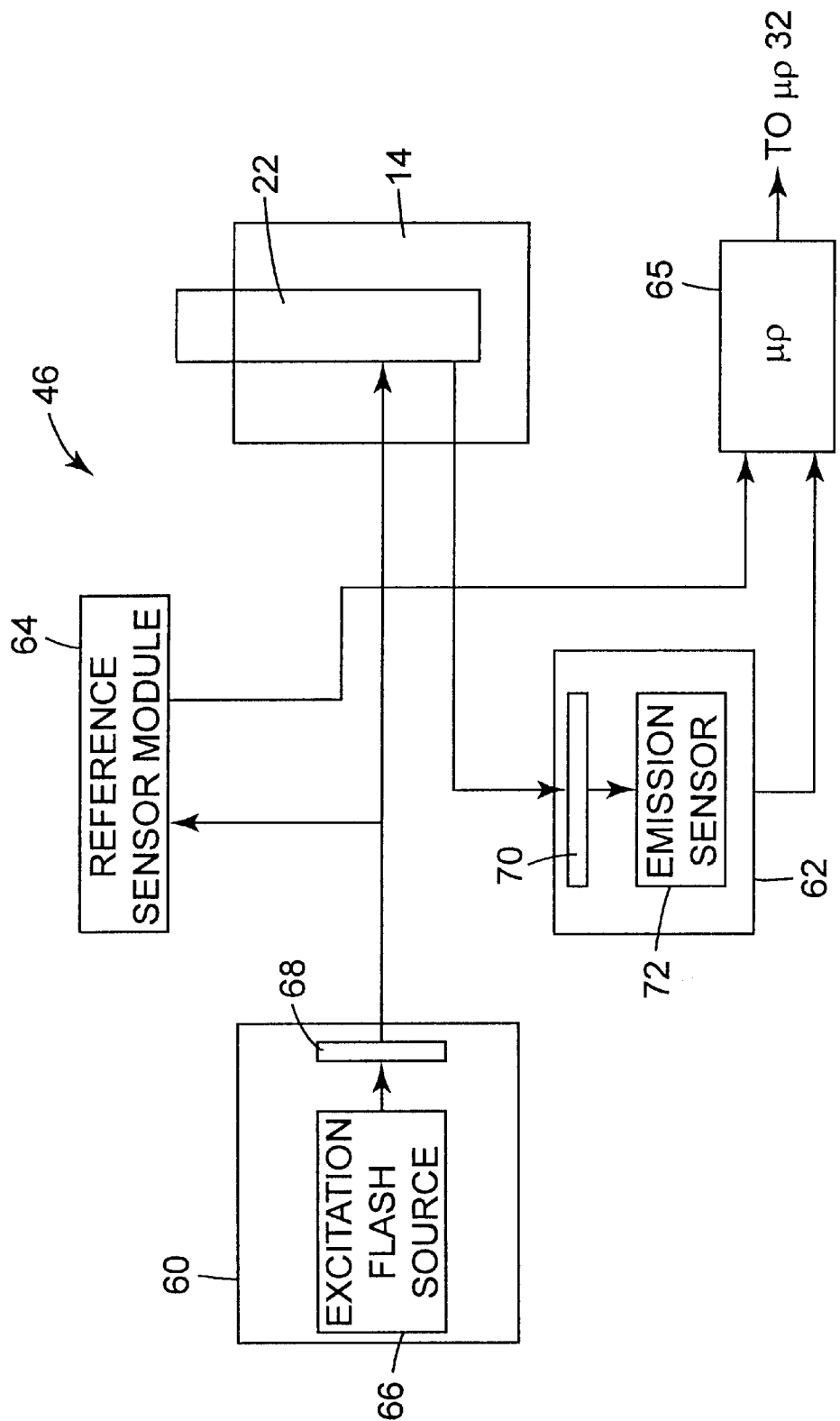
FIG. 3 is a more detailed block diagram of the flash/sensor circuit illustrated in FIG. 2.

FIG. 3 is a more detailed block diagram of florescence sensor circuit 46. Circuit 46 includes electro-optical excitation module 60, electro-optical sensing module 62, reference module 64 and microprocessor 65. FIG. 3 also shows an associated BI 22 and BI receiving well 14, proximate which florescence sensor circuit 46 is positioned.

In order to take a florescence reading from BI 22, electro-optical excitation module 60 provides optical excitation to the fluorescent substances in BI 22 and to reference module 64. Electro-optical excitation module 60 preferably includes excitation mechanism 66 and a filter 68. Excitation mechanism 66, in one preferred embodiment, is a flash tube (such as a xenon flash tube) which emits a broad band light pulse (as approximately a 100 μs pulse) which is rich in the near ultra-violet range of wavelengths. In another preferred embodiment, excitation mechanism 66 is a cold cathode fluorescent lamp (CCFL) which provides a continuous wave excitation source (such as a scintillated mercury arc lamp) and which is commercially available from JKL, Inc. of Pacoima, Calif. Other suitable excitation mechanisms can be used as well.

Filter 68 (which may be part of mechanism 66) is preferably an absorptive color glass filter which exhibits low auto-florescence and passes selected wavelengths. A suitable filter is a Schott BG 39, UG 11 filter which is available from Scott Glass Technologies, Inc. of Duryea, Pa. The light is passed through filter 68 and impinges on BI 22 and reference module 64. Where mechanism 66 is a CCFL, filtering may also be required to filter out sideband emissions.

Reference module 64 preferably includes a reference optical sensor and a filter (not separately shown). The filter is preferably a single filter, or a set of filters, which is chosen to pass the excitation energy which passes through filter 68. The filter in module 64 passes this energy to the reference optical sensor contained in module 64. A suitable filter is a Schott BG 39, UG 11 filter which is available from Scott Glass Technologies, Inc. of Duryea, Pa.

The reference optical sensor in module 64 senses the energy passing through the filter and provides a reference signal to microprocessor 65 which is indicative of the energy passing through the filter in module 64. The reference signal provided to microprocessor 65 is thus indicative of the intensity of the excitation energy emitted by excitation mechanism 66.

The light which is passed through filter 68 and impinges on BI 22 excites the fluorescent material in BI 22. The florescence exhibited by BI 22 is preferably collected by an integration cavity in BI well 14 which is preferably a geometric reflective cavity (such as a portion of a parabola, hyperbola or a sphere) arranged about BI 22 to collect (or integrate) the florescence emitted from BI 22 and to direct that florescence to electro-optical sensing module 62.

Electro-optical sensing module 62 includes filter 70 and optical sensor 72. Filter 70 is preferably a single filter, or a set of filters, which is chosen to reject surface reflection from the surface of BI 22 when the excitation energy impinges on the surface of BI 22. A suitable filter blocks light in approximately the 350 nanometer wavelength range and passes light in approximately the 450 nanometer wavelength range. Any suitable filtering can be used which tends to reduce interference between the excitation energy from excitation mechanism 66 and the fluorescent emission energy from BI 22. This filter acts to pass the emission wavelengths which are indicative of florescence in BI 22. One suitable filter used as filter 70 is provided by Schott Glass Technologies Inc. as a Schott BG 39, KV 408 filter. The output of filter 70 is provided to optical sensor 72 which is preferably a blue enhanced photodiode which enhances the sensitivity of the photodiode in the 400–450 nanometer wavelength range. One suitable optical sensor 72 is provided by Burr Brown Corporation of Tucson, Ariz. under the tradename OPT 301.

The output of optical sensor 72 is provided to microprocessor 65. In the preferred embodiment, microprocessor 65 includes associated memory and timing circuitry and amplifiers and other suitable conditioning circuitry for receiving the outputs from modules 62 and 64 and providing them as conditioned signals indicative of the intensity of excitation mechanism 66 and of the fluorescent activity in BI 22, respectively. Microprocessor 65 also preferably includes connection, through a flex circuit or other suitable circuit to microprocessor 32.

By providing both a reference sensor module 64, and optical sensor 72, a number of things are accomplished. First, the energy (e.g., light pulse) provided by excitation mechanism 66, in the embodiment where it is a flash tube, is not completely constant from flash-to-flash. In other words, the light output from excitation mechanism 66 is somewhat dependent on the temperature of the plasma arc in the lamp. Therefore, flashes can exhibit some variation in spectral content, from flash-to-flash. If a first flash is directed at BI 22, the fluorescent activity may be one level, while if a second flash (more intense than the first flash) is directed at the same BI 22, the fluorescent behavior of the substance in BI 22 may be different. By providing a reference optical sensor, the signal representing the fluorescent energy emitted by BI 22 can be normalized using the specific reference signal from reference module 64 which is indicative of the intensity of that particular flash from mechanism 66. Thus, the varying effects of different excitation intensities are substantially eliminated from further processing steps.

Also, the intensities of the emissions from excitation mechanism 66 can tend to degrade over time, and eventually excitation mechanism 66 becomes inoperative. By providing reference module 64, which is configured to sense the intensity of the energy from excitation mechanism 66, microprocessor 65 can be configured to provide a signal to microprocessor 32 which causes microprocessor 32 to alert the operator by using operator interface 19 when excitation mechanism 66 is no longer operating sufficiently.

Further, reference module 64 is also advantageous when used in conjunction with the BI presence sensors 52. When BI presence sensor 52 indicates that a BI is in place within well 14, microprocessor 32 can determine whether that particular well 14 is dirty or needs cleaning or other service. For example, when a BI 22 is not located in well 14, microprocessor 32 expects to see some type of autoflourescent behavior in response to a flash from flash mechanism 66. Also, reference module 64 is arranged to receive excitation energy reflected from well 14 (rather than directly from filter 68) microprocessor 32 can compare the expected results of a flash (or excitation) with the actual results of a flash to determine whether a foreign object is located in well 14, whether the walls of well 14 are coated with debris or otherwise need cleaning, or whether well 14 needs some other type of service.

Figure 4:
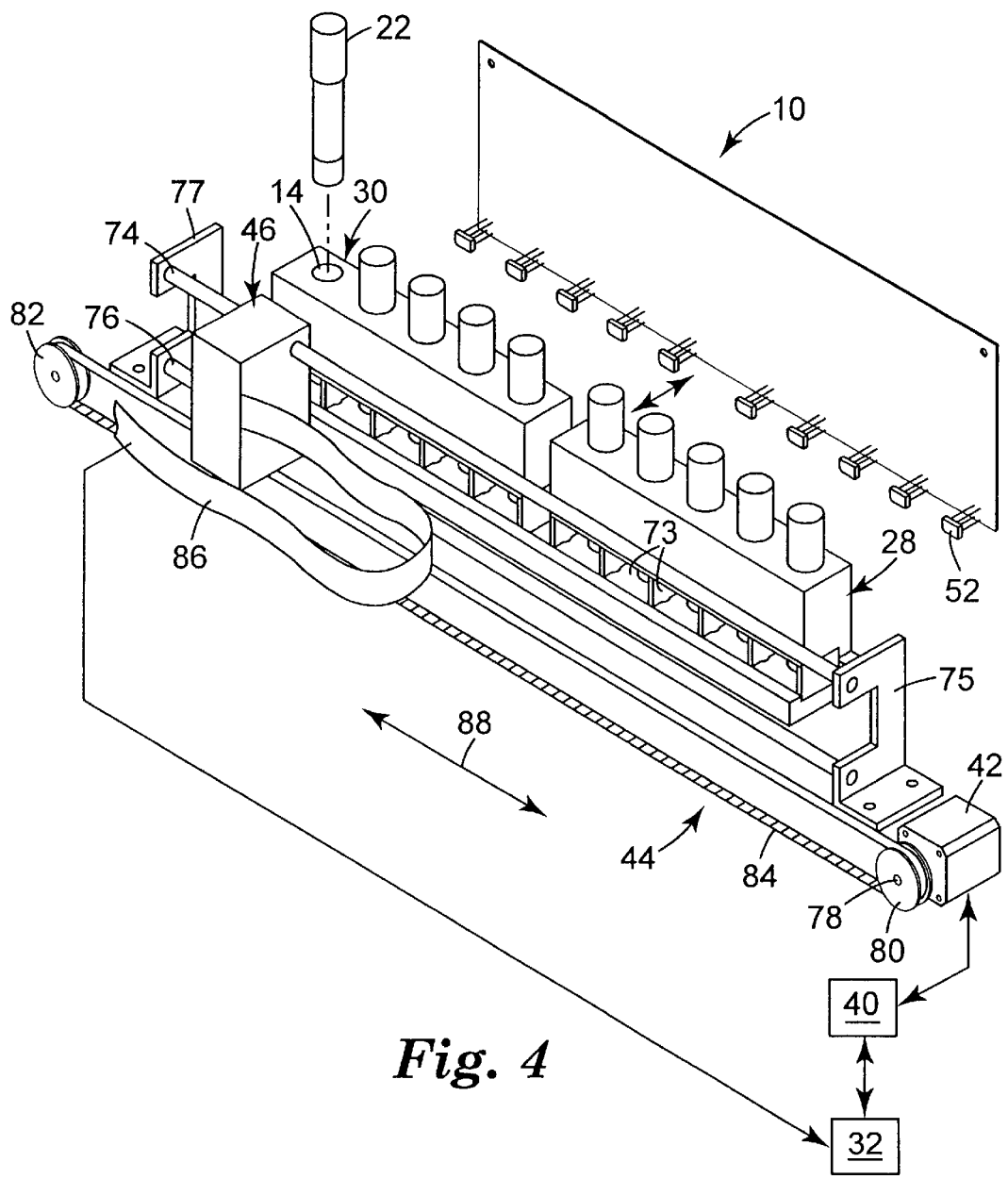
FIG. 4 illustrates one embodiment of a carriage assembly in accordance with one aspect of the present invention.

FIG. 4 is a partially exploded view of a portion of reading apparatus 10 with housing 12 removed. FIG. 4 better illustrates the configuration of one preferred embodiment of drive mechanism 44. Similar items to those shown in FIGS. 1 and 2 are similarly numbered. FIG. 4 illustrates that florescence sensor circuit 46 is mounted to a pair of linear slides 74 and 76. FIG. 4 also illustrates that BI receiving wells 14 have openings 73 therein. Openings 73 expose a lower portion of BI 22 to fluorescence sensing circuit 46. Slides 74 and 76 are arranged in generally parallel relation to one another, are mounted to opposing brackets 75 and 77, and extend along the plurality of BI receiving wells 14.

FIG. 4 also illustrates that stepper motor 42 has a drive output 78 which is coupled to a first pulley 80. In a preferred embodiment, first pulley 80 is a cogged wheel which is supported for rotation with drive output 78 of stepper motor 42. A second, idler pulley 82 is mounted for idler rotation. Pulleys 80 and 82 are coupled to one another by cogged belt 84. Thus, as microprocessor 32 controls stepper motor 42 (through stepper motor controller 40) to rotate, drive output 78 drives pulley 80 which, in turn, drives cogged belt 84. Belt 84 is supported for rotation by idler pulley 82, and is fixably coupled to fluorescence sensing circuit 46. Stepper motor 42 also includes a position sensor which senses the relative position of drive output 48, as it rotates. This position signal is provided to controller 40 and microprocessor 32. In this way, microprocessor 32 can drive fluorescence sensor circuit 46 along generally parallel linear slides 74 and 76, to various positions closely proximate openings 73 in BI receiving wells 14 in order to take florescence measurements from each of BI receiving wells 14.

FIG. 4 also illustrates that fluorescence sensing circuit 46 is preferably coupled to microprocessor 32 through the use of a flex circuit 86. Flex circuit 86 is preferably any suitable, commercially available flexible circuit which will accommodate the linear movement of fluorescence sensing circuit 46 generally in a direction indicated by arrow 88, while still maintaining electrical contact with microprocessor 32.

In addition, FIG. 4 also illustrates one preferred implementation of BI presence sensors 52. In the preferred embodiment, BI presence sensors 52 are mounted to a back plate (or printed circuit board) 90 which is positioned closely proximate a portion of BI receiving well 14 opposite opening 73. In addition, a second opening (or passageway) is provided in BI receiving well 14 generally opposite opening (or passageway) 73. BI presence sensors 52 are preferably infra-red sensors which include both an infra-red emitter, and an infra-red detector. Presence sensors 52 are arranged closely proximate the second opening in BI well 14 (as shown in greater detail with respect to FIG. 7) such that the infra-red emitter can impinge infra-red radiation into BI receiving well 14 through the second passageway. If infra-red radiation is reflected back, that indicates that a BI 22 is located within BI receiving well 14, and presence sensor 52 provides a suitable output to microprocessor 32. However, if an expected amount of infra-red radiation is not reflected back, then the infra-red detector does not sense the appropriate level of reflected infra-red radiation. This indicates that no BI 22 resides in that particular BI receiving well 14. Again, the particular presence sensor 52 provides a suitable signal to microprocessor 32 indicating that no BI 22 is present.

Figure 5:
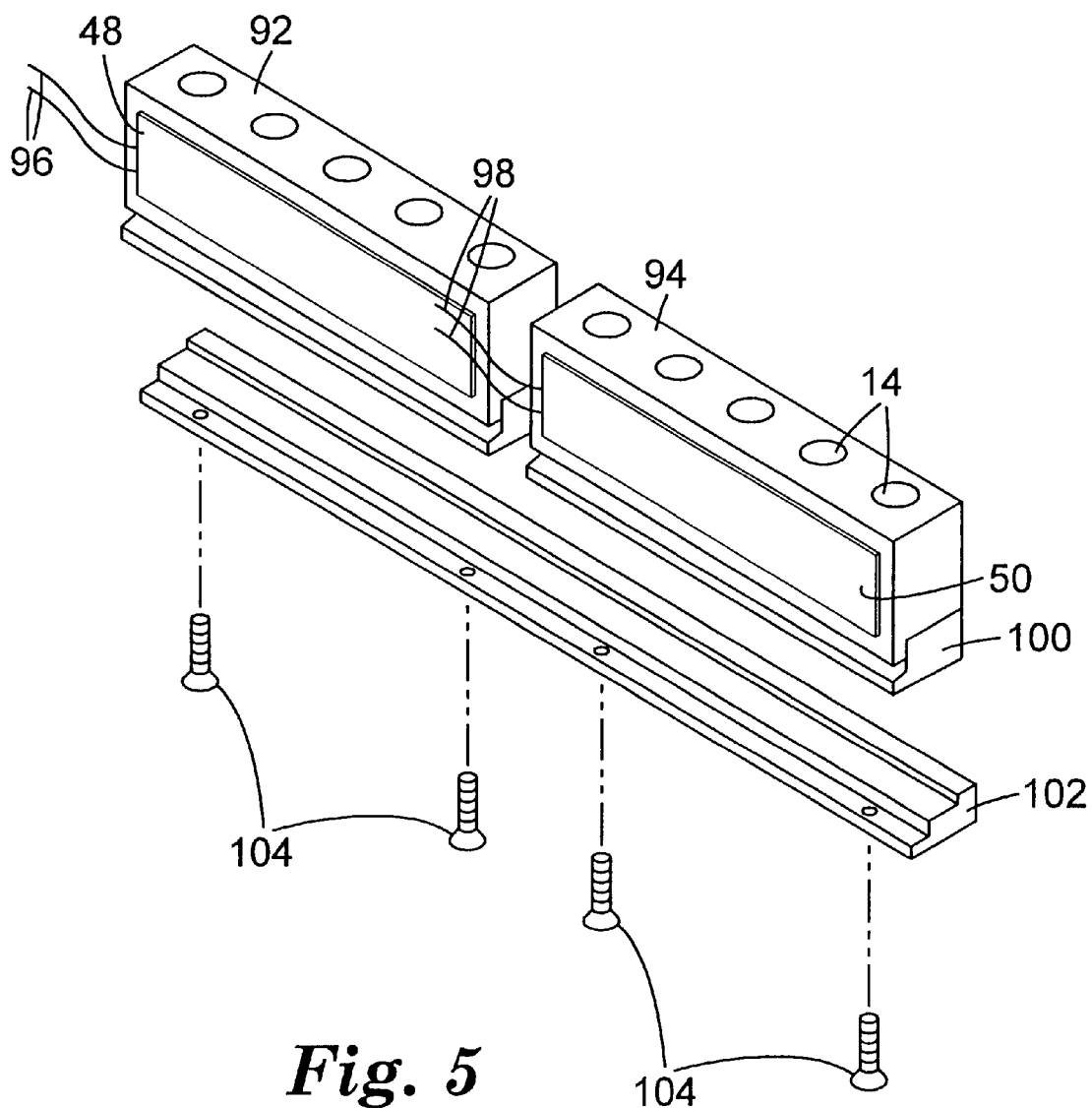
FIG. 5 illustrates one embodiment of a heater configuration in accordance with one aspect of the present invention.

FIG. 5 better illustrates the configuration of a preferred configuration of heaters 48 and 50 in accordance with the present invention. In one preferred embodiment, BI receiving wells 14 are preferably defined by, or arranged closely adjacent, blocks 92 and 94 of thermally conductive material. Heaters 48 and 50 are commercially available resistance elements or other suitable heater devices which are coupled to blocks 92 and 94 by a highly thermally conductive connection (such as an integral contact type of connection with screws or another suitable connective device) that brings heaters 48 and 50 into integral contact with blocks 92 and 94 or through the use of a highly thermally conductive intermediate mechanism.

Heaters 48 and 50 have conductors 96 and 98, respectively, connected thereto. Conductors 96 and 98 are also connected to conventional heater power and control circuits, which are, in turn, controlled by microprocessor 32. The heater power and control circuits provide power over conductors 96 and 98 to heaters 48 and 50 to cause heaters 48 and 50 to heat up under the control of microprocessor 32. Heaters 48 and 50 are also provided with thermocouples, thermistors, or other suitable heat sensing devices which are in closely adjacent contact with either heaters 48 and 50 or thermally conductive blocks 92 and 94. The heat sensing devices are also electrically coupled to microprocessor 32. The heat sensing devices provide a signal to microprocessor 32 which is indicative of the heat of thermally conductive blocks 92 and 94 such that microprocessor 32 can control heaters 48 and 50 in a closed loop fashion.

FIG. 5 also illustrates that blocks 92 and 94 are preferably coupled to brackets 75 and 77 (or other suitable structural support portion of housing 12) through intermediate brackets 100 and 102 by suitable fasteners such as screws 104. In the preferred embodiment, brackets 100 and 102 are formed of material that has a very low thermal conductivity relative to blocks 92 and 94. Further, in the preferred embodiment, blocks 92 and 94 are spaced relative to one another by either an air gap or a sufficiently thermally insulative material such that there is no significant heating of one of blocks 92 and 94 by the heater associated with the other of blocks 92 and 94 when the two are heating to different temperatures. In this way, tighter heating control can be maintained over blocks 92 and 94.

Figure 6:
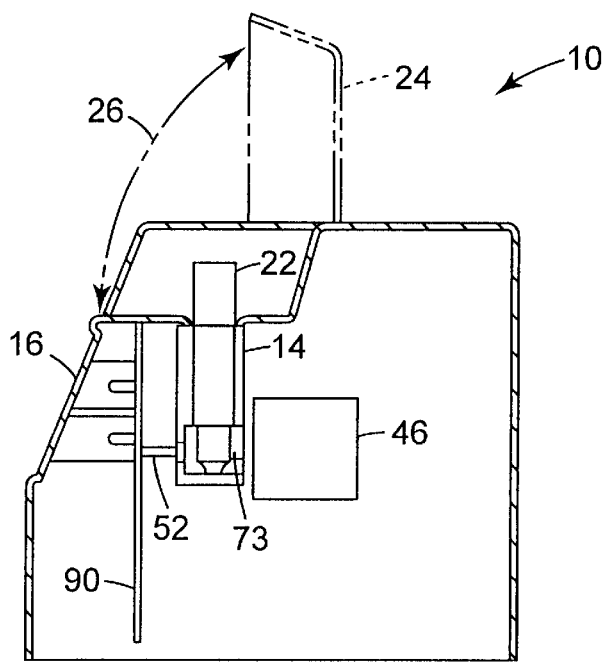
FIG. 6 is a side, partially sectional view of the biological indicator reading apparatus shown in FIG. 1.

FIG. 6 better illustrates one preferred placement and configuration of BI 22 and various components of apparatus 10 relative to housing 12. FIG. 6 illustrates that in one preferred embodiment, BI presence detector 52 is located in a forward portion of housing 12 relative to BI 22, while fluorescence sensor circuit 46 and its associated slides, motor, and belt drive are located in a rearward portion of housing 12 relative to BI 22. Of course, any other suitable configurations can also be used.

Figure 7:
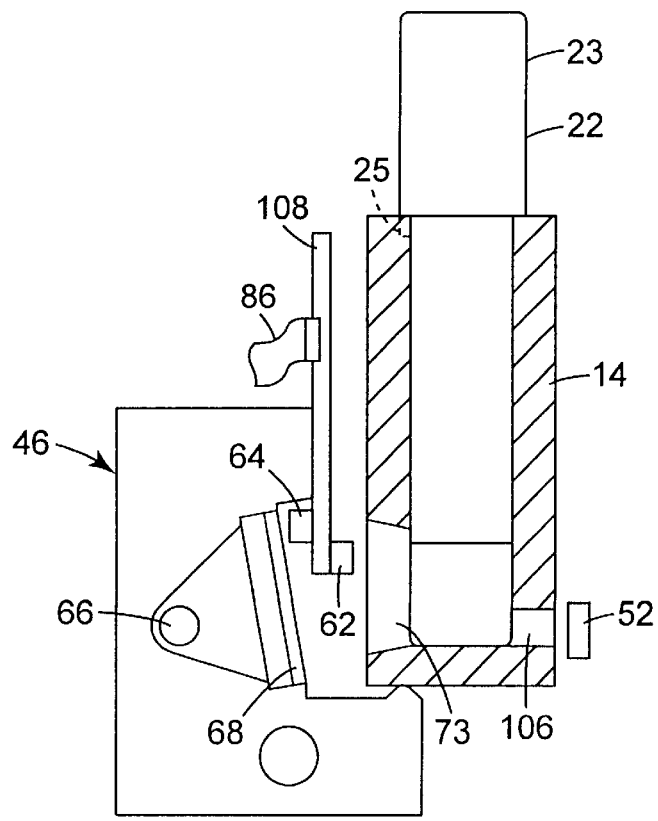
FIG. 7 is a greatly enlarged view illustrating a BI and fluorescence sensors in accordance with one aspect of the present invention.

FIG. 7 is a greatly enlarged depiction of one preferred arrangement of presence sensor 52, BI receiving well 14, and fluorescence sensor circuit 46. FIG. 7 illustrates the second passageway 106 through the wall of BI receiving well 14. Passageway 106 is preferably located at a lower-most portion of well 14, and BI presence sensor 52 is located closely proximate passageway 106. In this way, presence sensor 52 provides a signal to microprocessor 32 indicating that BI 22 is not present in well 14, unless BI 22 is properly seated all the way into well 14, toward the bottom of well 14.

FIG. 7 also indicates one optional feature of BI 22. In one preferred embodiment for reading BI 22, fluorescence sensor circuit 46 takes fluorescence readings based upon fluorescence emitted from a small portion of the surface of BI vessel 22 facing circuit 46. In that case, it is important that for subsequent readings, BI 22 remains in the same orientation within well 14. Therefore, in one preferred embodiment, in accordance with the present invention, BI 22 is provided with a cap 23 which has an antirotational feature 25 thereon. Antirotational feature 25, in one preferred embodiment, is simply a tab or protrusion which extends away from the surface of cap 23. Also, well 14 is formed to define a protrusion receiving notch. The angular orientation of BI 22 about its longitudinal axis must thus be the same in order for BI 22 to be completely received and nested within well 14. Therefore, during every subsequent reading of BI 22 by circuit 46, the angular orientation of BI 22 will be substantially identical.

However, in another preferred embodiment, the wall of well 14, at least in the area of passageway 73 and extending about substantially the entire periphery of BI 22 in that area, is formed of reflective material having a geometric shape which tends to reflect fluorescence emitted by BI 22 toward passageway 73. One such geometric configuration is a portion of a parabola, while another such configuration may be a portion of a sphere. Other suitable geometric configurations can also be used. In that case, the fluorescence emitted by substantially the entire periphery of BI 22 in the area of passageway 73 is collected or integrated and directed toward the photo sensors in circuit 46. Thus, it may not be as crucial to have the antirotational feature 25 on cap 23.

In any case, whether circuit 46 is reading fluorescence from only a small portion of the exterior of BI 22, or whether it is reading fluorescence reflected about substantially the entire lower periphery of BI 22, circuit 46 is preferably provided with a circuit board 108 to which electro-optical reference module 64 and electro-optical sensing module 62 are mounted. FIG. 7 illustrates the preferred embodiment of mounting modules 62 and 64. Module 64 is preferably mounted on a rearward side of circuit board 108, relative to BI 22, such that it faces excitation mechanism 66 but is on an opposite side of filter 68 from excitation mechanism 66. Further, module 62 is preferably mounted on the forward side of circuit board 108, relative to BI 22 such that it faces passageway 73. In this way, electro-optical reference module 64 will be arranged to readily receive excitation energy from lamp 66 after it passes through filter 68, but it will be substantially shielded from receiving fluorescent emission energy from BI 22. Similarly, electro-optical sensing module 62 is positioned such that it does not directly receive the excitation energy from excitation mechanism 66, but it is positioned to readily receive emission energy from BI 22. Of course, and as indicated previously in the specification, modules 62 an 64 both preferably include electro-optical sensor circuits, as well as suitable filtering to enhance sensing of desired wavelengths.

Figure 8A:
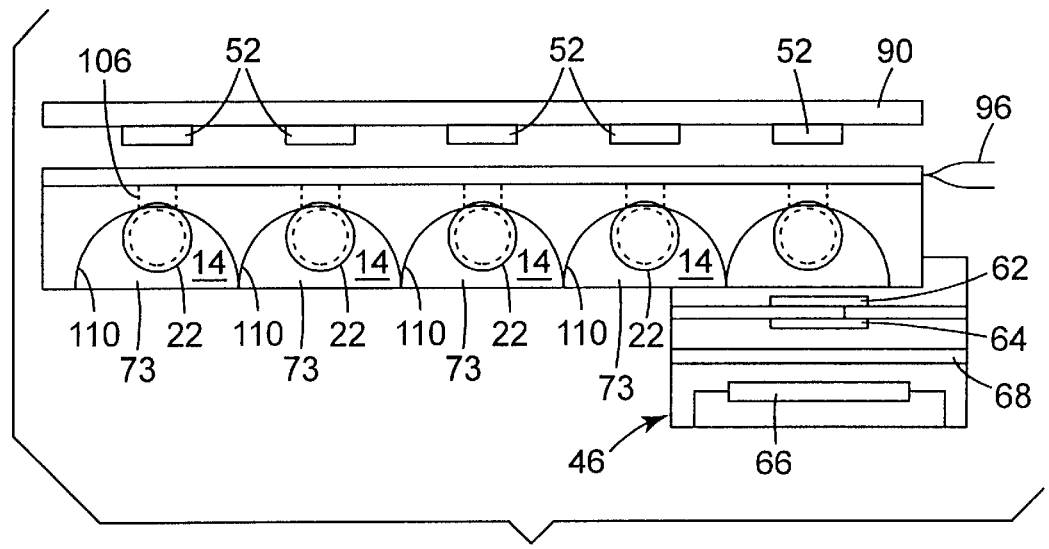
FIGS. 8A and 8B show a top view of a portion of the biological indicator reading apparatus shown in FIG. 1.

FIG. 8A is a partial sectional top view of block 92, illustrating the placements of BI presence sensors 52, BI receiving wells 14, and fluorescence sensor circuit 46. Similar items are similarly numbered to those shown in previous figures. FIG. 8A also better illustrates one preferred embodiment of the shape of BI receiving wells 14 in the area of passageway 73. BI receiving wells 14 are shown defined by a wall 110 in that area. Wall 110 is preferably formed of a reflective material, such as a mirrored material or other suitable reflective material, and is formed in a hemispherical shape (or in a shape corresponding to another portion of a sphere). FIG. 8A illustrates BI 22 lying against the base of a spherically shaped portion of well 14. However, BI 22 could also be placed in another region relative to well 14, such as at a point spaced away from the base of the spherical wall of well 14.

Figure 8B:
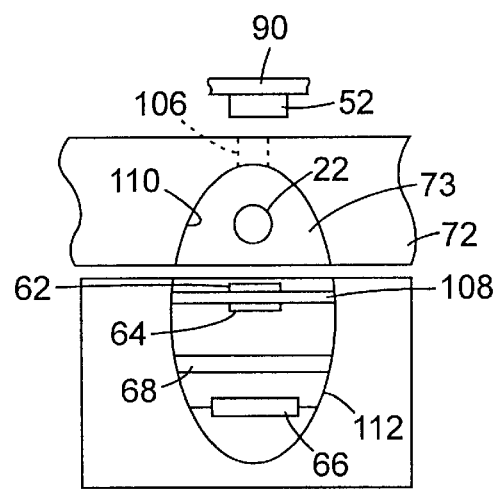

FIG. 8B shows a greatly enlarged view of another arrangement of BI receiving well 14 and circuit 46 in accordance with the present invention. Similar items are similarly numbered to those shown in FIG. 8A. In FIG. 8B, well 14 is shown having wall 110 formed of reflective material and formed as a portion of a parabola. Also, BI 22 is spaced from the base of the parabolic section and is located substantially centered at one focus of the parabola. Also, FIG. 8B illustrates that the excitation mechanism 66 in circuit 46 is housed within a chamber which is defined by wall 112. Wall 112 is substantially parabolic in shape, as well, and is configured as a parabolic section which substantially completes the parabolic section of wall 110. Excitation mechanism 66 is spaced from the base of the parabolic section defined by wall 112 and is preferably located at the other focus of the parabola, opposite that at which BI 22 is located. Many other suitable shapes, such as ellipses, complex curves, or other suitable shapes or contours, can be used, as well.

Figure 9:
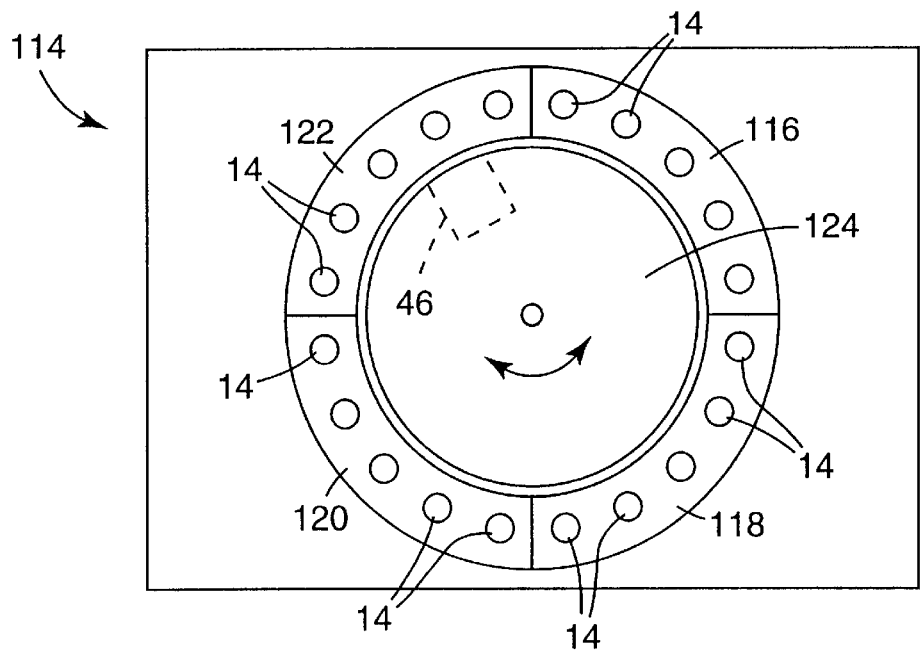
FIG. 9 is a top view illustrating another embodiment of a biological indicator reading apparatus in accordance with the present invention.

FIG. 9 is a top view of another preferred embodiment for implementing a biological indicator reading apparatus in accordance with the present invention. FIG. 9 illustrates reading apparatus 114, Reading apparatus 114 is provided with four incubator zones 116, 118, 120, and 122. Each incubator zone has a plurality of BI receiving wells 14 disposed therein.

Since there are four incubator zones, four heaters are provided such that reader 114 can be configured to heat to up to four different temperatures to accommodate up to four different types of BIs which require different incubation temperatures. Portions of the incubator zones are preferably color-coded to match the cap color for the particular type of BI being used. The operator can then simply match the cap color of the BI 22 with the color of the incubator zone to ensure that the BI 22 is placed in the proper incubation zone for appropriate incubation.

Incubator zones 116, 118, 120, and 122 are arranged annularly about a centrally located, rotatable reading turret 124. Reading turret 124 contains fluorescence sensor circuit 146. Each reading well 14 has an associated BI presence sensor 52. As soon as the operator places the BI 22 into one of the wells 14, reading turret 124 is indexed to a position such that a fluorescence sensor circuit is arranged closely proximate that BI receiving well 14 so that fluorescence readings can be taken. In a preferred embodiment, the angular position of reading turret 124 is tracked and maintained by microprocessor 32. Therefore, reading turret 124 can be rotated circularly in opposite directions to access the various reading wells 14 in incubator zones 116, 118, 120, and 122. Preferably, microprocessor 32 controls reading turret 124 such that it does not rotate more than 360° or about another suitable arc (to avoid twisting and tangling of flex circuit 86).

Figure 10:
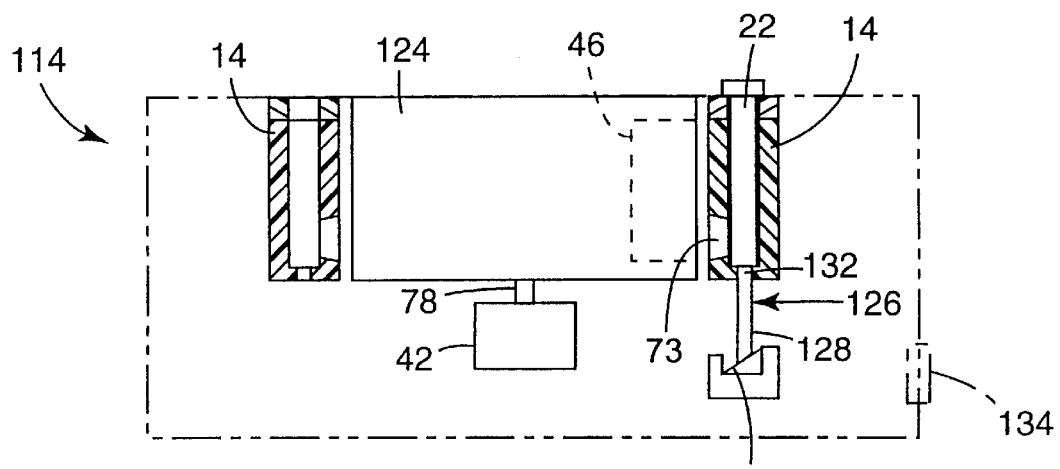
FIG. 10 is a side, partially sectional view of the biological indicator reading apparatus shown in FIG. 9.

FIG. 10 is a side sectional view of a portion of reading apparatus 114. FIG. 10 illustrates that stepper motor 42 is preferably arranged at the bottom of reading turret 46 and has its drive output 78 coupled thereto. Microprocessor 32 thus controls stepper motor 42 to access one of the passageways 73 associated with a reading well 14 which is populated with a BI 22.

FIG. 10 also illustrates another embodiment for a BI presence sensor 126. Presence sensor 126, illustrated in FIG. 10, includes reciprocable actuating rod 128 and switch sensor 130. Actuating rod 120 has a first end 132, which protrudes into well 114 beyond the bottom surface thereof. Rod 128 is preferably biased by a spring or other suitable bias member (not shown) into an upwardly projecting position. When the operator properly seats BI 22 in well 14, the bottom portion of BI 22 contacts the upper portion 130 of actuating rod 128, causing actuating rod 128 to lower into a lowered position, which depresses switch sensor 130. Switch sensor 130 then provides a signal to microprocessor 32 indicating that the particular well 14 is now populated with BI 22. FIG. 10 also illustrates a serial port 134 which is preferably coupled to microprocessor 32 for asynchronous communication with other devices such as a server, etc., as described with respect to FIG. 2.

Figure 11:
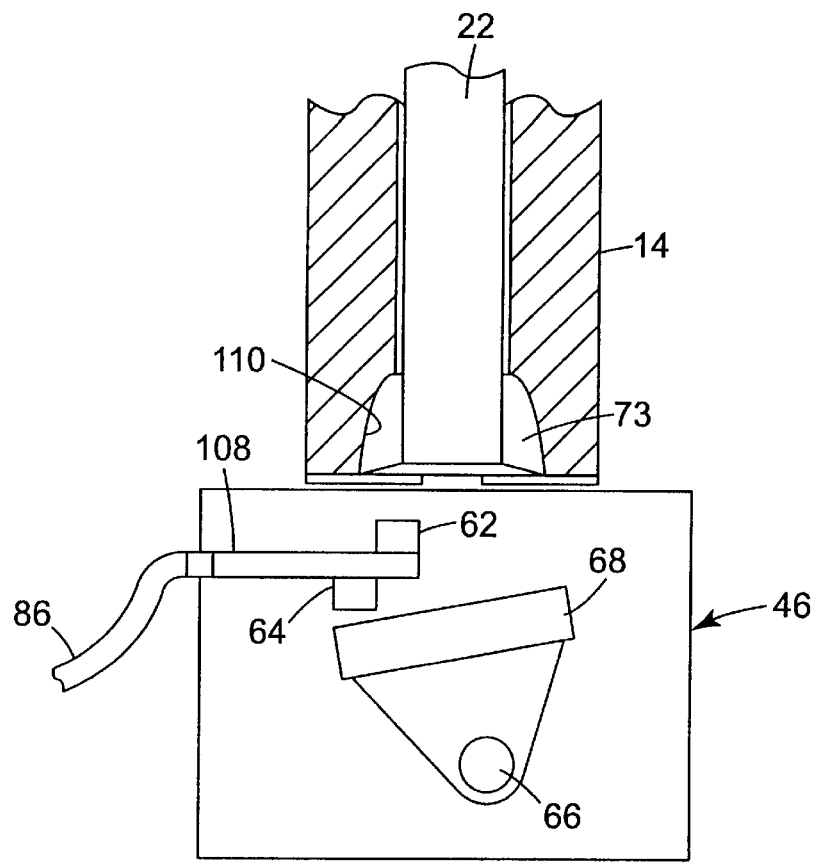
FIG. 11 illustrates a second embodiment of an integration cavity in accordance with one aspect of the present invention.

FIG. 11 illustrates another preferred configuration for well 14. Well 14 shown in FIG. 11 is similar to BI receiving wells 14 described with respect with the previous figures except that passageway 73 is provided in the bottom of well 14 shown in FIG. 11. Reflective surface 110, shown in FIG. 11, is thus a surface formed of a reflective material and shaped in a geometric shape which reflects the fluorescence emitted by BI 22 downward toward fluorescence sensor circuit 46 so that the fluorescence emitted by BI 22 is integrated and collected and directed in the downward direction through passage 73, rather than sideways, relative to BI 22. Of course, the reflective surface can be formed in any suitable geometric shape.

Figure 12:
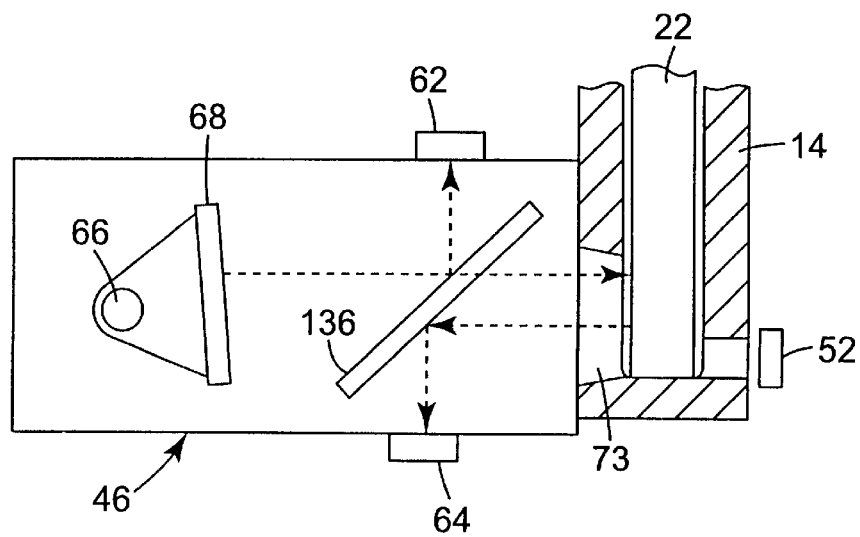
FIG. 12 is a partially schematic view illustrating the configuration of a fluorescence sensor in accordance with one aspect of the present invention.

FIG. 12 illustrates another preferred embodiment for the arrangement of sensor modules 62 and 64. Similar items are similarly numbered to those shown in previous figures. BI receiving well 14, illustrated in FIG. 12, can be similar to that shown in FIGS. 7–8B, wherein fluorescence emitted by BI 22 is directed sideways relative to BI 22, or it can be of the type illustrated in FIG. 11, in which the fluorescence emitted from BI 22 is emitted downwardly relative to BI 22, toward fluorescence sensor circuit 46. In either case, rather than positioning modules 62 and 64 on opposite sides of the printed circuit board or other support member 108, modules 62 and 64 are positioned outwardly, out of the direct path of radiation from excitation mechanism 66. Thus, the sensors are not blocking ballistic photons from impinging on the target.

Instead, a dichroic reflector 136 is positioned relative to excitation mechanism 66 and passageway 73 such that it reflects light of different wavelengths toward the different modules 62 and 64. In the preferred embodiment, dichroic reflector 136 is formed to direct a portion of the excitation radiation from excitation mechanism 66 (preferably about 4%) toward module 62. Dichroic reflector 136 is also preferably formed to direct the emission radiation (i.e., the fluorescence radiation) from BI 22 toward module 64. Thus, dichroic reflector 136 preferably directs a portion of the excitation frequency, which will typically be on the order of 350 nm, toward module 62 such that module 62 can provide the desired reference signal. Dichroic reflector 136 also directs the emission radiation, which will be on the order of approximately 450 nm, toward sensor module 64 such that module 64 can sense the fluorescence emitted by BI 22 and provide the desired sensor signal. Other suitable configurations can also be used.

In any of the above-described embodiments, the operator preferably cracks the ampule in BI 22 prior to placing it in BI receiving well 14. BI presence sensors 52, 126 then provide a signal to microprocessor 132, indicating that a BI receiving well 14 has been populated. Microprocessor 32 then controls stepper motor 32 to position fluorescence sensor circuit 46 proximate the populated BI well. After a desired wet-out period (i.e., after the ampule has been broken and the BI has been adequately wet out) a baseline reading indicative of the autofluorescent behavior of the BI is taken. Then, preferably at fixed time intervals thereafter, subsequent fluorescence readings are taken to establish the desired kinetic characteristics for that particular BI 22 (i.e., the fluorescence/time profile is generated) in order to determine the efficacy of the sterilization cycle associated with that BI 22.

It should also be noted that the heaters in the incubation zones of the present apparatus can be set to heat to a desired temperature in hardware by using dip switches or another suitable hardware mechanism. It is preferred, however, that the heaters be software configurable, as described above.

Also, in the preferred embodiment, where the EI presence sensor is an electro-optic sensor, such as an infrared detector, the radiation source of the detector is shut off during fluorescence measurements. This helps to eliminate any errors associated with extraneous radiation entering well 14. Also, the preferred spacing of the circuit 46 from well 14 is approximately 1 mm. However, any suitable distance which reduces the amount of stray light entering well 14 can be used. Also, in one preferred embodiment, as soon as system 10 or system 14 is powered up, microprocessor 32 cycles through each of the BI presence sensors to determine whether any of wells 14 are populated with BIs. This continues on an intermittent basis until microprocessor 32 detects the presence of a BI in a well 14. Then, processing of that BI begins. BIs can be added asynchronously, and separate kinetic profiles can be kept for each, regardless of when the kinetic profile for other BIs 22 was started.

Thus, it can be seen that the present biological indicator reading apparatus provides a number of significant advantages. The number of steps during which the operator must handle the particular BI 22 is significantly reduced over prior methods. In addition, many different BIs can be asynchronously processed without cumbersome record keeping and logging on the part of the operator. Further, since a plurality of different heating and incubation zones are provided, different types of BIs can be simultaneously processed in an efficient manner. Also, since, the BI receiving well 14 is configured to collect fluorescence emitted by BI 22 (in one preferred embodiment) the signal from the fluorescence sensor has a much greater amplitude than in prior systems. This reduces the amount of additional amplification which is required and also increases the signal-to-noise ratio associated with the sensor signal.

Although the present invention has been described with reference to preferred embodiments, workers skilled in the art will recognize that changes may be made in form and detail without departing from the spirit and scope of the invention.

What is claimed is:

1. An apparatus for reading a plurality of biological sterilization indicators (BIs) to determine the efficacy of a plurality of sterilization cycles, each BI capable of exhibiting fluorescence to indicate a non-lethal sterilization cycle, the apparatus comprising:

plurality of biological sterilization indicator holders each configured to receive one of the biological sterilization indicators;

carriage controllably movable relative to the plurality of biological sterilization indicator holders to positions proximate each of the biological sterilization indicator holders;

radiation emitter mounted on the carriage and positioned to impinge radiation on a biological sterilization indicator received in a selected biological sterilization indicator holder when the carriage is in the position proximate the selected biological sterilization indicator holder;

fluorescence sensor mounted on the carriage and positioned to sense fluorescence exhibited by the biological sterinization indicator in the selected biological sterilization indicator holder in response to the radiation impinged thereon and to provide a fluorescence signal indicative of the sensed fluorescence; and controller coupled to the fluorescence sensor to receive the fluorescence signal and to provide an output signal indicative of the fluorescence sensed, the controller being configured to control the position of the carriage to intermittently position the carriage proximate each of he biological sterilization indicator holders then holding a biological sterilization indicator and to receive the fluorescence signal indicative of the fluorescence sensed from the biological sterilization indicator corresponding to the biological sterilization indicator holder proximate which the carriage is then positioned;

said controller having a means for determining the adequacy of a sterlization cycle based on the fluorescence signal from the fluorescence sensor.

2. The apparatus of claim 1 and further comprising a memory, coupled to the controller, the controller being configured to store, in the memory, data indicative of the fluorescence of each biological sterilization indicator based on the fluorescence signals received.

3. The apparatus of claim 2 and further comprising:

an output device, coupled to the controller, configured to provide operator perceptible indicia indicative of the efficacy of the plurality of sterilization cycles based on the data stored in the memory.

4. The apparatus of claim 3 wherein the output device comprises a plurality of displays, one display associated with each biological sterilization indicator holder, each of the plurality of displays providing an indication of the efficacy of one of the plurality of sterilization cycles associated with the biological sterilization indicator received in the biological sterilization indicator holder associated with the display.

5. The apparatus of claim 1 wherein the fluorescence sensor comprises:

photo sensor positioned to receive the fluorescence exhibited by the biological sterilization indicator and to provide a sensor signal indicative of the sensed fluorescence; and sensor controller coupled to the photo sensor to receive the sensor signal and coupled to the controller and configured to provide the fluorescence signal based on the sensor signal.

6. The apparatus of claim 5 wherein the sensor controller is coupled to the radiation emitter to control the radiation emitter.

7. The apparatus of claim 5 wherein the fluorescence sensor further comprises:

a reference sensor coupled to the sensor controller and positioned to sense radiation emitted from the radiation emitter and to provide a reference signal to the sensor controller based on the radiation sensed, the sensor controller being configured to provide the fluorescence signal based on the reference signal.

8. The apparatus of claim 5 wherein each of the plurality of biological sterilization indicator holders includes an inner wall surface having a receiving aperture therein for receiving the associated biological sterilization indicator and a first sensing passageway therethrough, the photo sensor being positioned relative to the first sensing passageway to receive fluorescence emitted from the associated biological sterilization indicator which passes through the sensing passageway.

9. The apparatus of claim 8 and further comprising a plurality of vessel presence detectors coupled to the controller, one of the plurality of vessel presence detectors being associated with each of the plurality of biological sterilization indicator holders and providing a presence signal indicative of whether a biological sterilization indicator is present in the associated biological sterilization indicator holder.

10. The apparatus of claim 9 wherein each of the plurality of vessel presence detectors comprises:

an emitter coupled to the controller and positioned proximate an associated biological sterilization indicator holder to impinge radiation on a biological sterilization indicator received in the associated biological sterilization indicator holder; and a detector coupled to the controller and positioned proximate the associated BI holder to conditionally detect the radiation and provide the presence signal based on radiation detected.

11. The apparatus of claim 10 wherein the inner wall includes a second sensing passageway therethrough, the detector of the associated vessel presence sensor being positioned to detect light emitted by the emitter and passing through the second sensing passageway.

12. The apparatus of claim 11 wherein each biological sterilization indicator holder has an end generally opposite the receiving aperture and wherein the second sensing passageway is located closer to the end than to the receiving aperture.

13. The apparatus of claim 9 and further comprising:

a motor; and a linkage coupled to the motor and the carriage, the motor being configured to drive movement of the carriage through the linkage.

14. The apparatus of claim 13 wherein the controller includes a motor controller, coupled to the motor to control the motor, the controller being configured to control the motor to move the carriage to a position proximate a biological sterilization indicator holder in response to the presence signal from the vessel presence detector associated with the biological sterilization indicator holder indicating that a biological sterilization indicator is in the associated biological sterilization indicator holder.

15. The apparatus of claim 8 wherein the inner surface is formed with a reflective portion arranged to reflect at least a portion of the fluorescence emitted by the biological sterilization indicator in the biological sterilization indicator holder toward the first sensing passageway.

16. The apparatus of claim 15 wherein the reflective portion is generally parabolic.

17. The apparatus of claim 15 wherein the reflective portion is generally hemispherical.

18. The apparatus of claim 8 wherein the photo sensor includes:

a filter system configured to filter radiation other than wavelengths approximately associated with the fluorescence.

19. The apparatus of claim 1 and further comprising:

a first heater;

a second heater;

wherein the plurality of biological sterilization indicator holders comprises a first plurality of biological sterilization indicator holders mounted operably proximate the first heater to receive heat from the first heater, and a second plurality of biological sterilization indicator holders mounted operably proximate the second heater to receive heat from the second heater.

20. The apparatus of claim 19 wherein the first heater is configured to heat the first plurality of biological sterilization indicator holders to a first temperature and wherein the second heater is configured to heat the second plurality of biological sterilization indicator holders to a second temperature, different from the first temperature.

21. The apparatus of claim 20 and further comprising:
an operator input device coupled to the controller and configured to receive operator inputs and provide an operator input signal based on the operator inputs; and
wherein the first and second heaters are configured to receive respective temperature input signals indicative of the first and second temperatures and to heat the first and second plurality of biological sterilization indicator holders to the first and second temperatures, respectively, based on the temperature input signals, and wherein the first and second heaters are coupled to the controller, the controller being configured to receive the operator input signal indicative of the first and second temperatures and provide the temperature input signal to the first and second heaters, respectively, based on the operator input signal.

22. An apparatus for reading a plurality of biological sterilization indicators (BIs) to determine the efficacy of one or more sterilization cycles, the biological sterilization indicators capable of exhibiting fluorescence to indicate a non-lethal sterilization cycle, the apparatus comprising:
a plurality of holders, each holder configured to receive one of the plurality of biological sterilization indicators, each holder including a passage exposing a portion of the biological sterilization indicator received therein;
heater coupled to the plurality of holders to heat the plurality of holders to at least one preselected temperature;
carriage moveable relative to the plurality of holders among positions proximate each of the plurality of holders;
radiation source, mounted on the carriage for movement with the carriage and configured to be operably aligned with the passage in a selected holder of the plurality of holders, when the carriage is in a position proximate the selected holder, to emit radiation through the passage in the selected holder;
fluorescence sensor mounted on the carriage for movement with the carriage and configured to sense fluorescence exhibited by the biological sterilization indicator in the selected holder, through the passage in the selected holder, and to provide a sensor signal indicative of the sensed fluorescence; and
first controller, mounted to the carriage for movement with the carriage and coupled to the fluorescence sensor and the radiation source, the first controller being configured to receive the sensor signal and provide a fluorescence signal based on the sensor signal;
said controller having a means for determining the adequacy of a sterilization cycle based on the fluorescence signal from the fluorescence sensor.

23. The apparatus of claim 22 and further comprising:
a second controller coupled to the first controller; and
memory, coupled to the second controller, the second controller being configured to receive fluorescence signals from the first controller associated with a plurality of biological sterilization indicators and store data indicative of the fluorescence signals in the memory to thus store a kinetic response profile associated with each biological sterilization indicator, the kinetic response profiles for each BI being stored asynchronously with one another.

24. The apparatus of claim 23 and further comprising a motor coupled to the carriage to drive the carriage among the positions proximate the biological sterilization indicator holders.

25. The apparatus of claim 24 and further comprising a biological sterilization indicator presence sensor coupled to the biological sterilization indicator holders to sense presence of a biological sterilization indicator in the biological sterilization indicator holders and to provide a biological sterilization indicator presence signal indicative of whether a biological sterilization indicator is present in the biological sterilization indicator holder.

26. The apparatus of claim 25 wherein the biological sterilization indicator presence sensor comprises:
an infrared emitter positioned to emit infrared radiation toward a portion of the biological sterilization indicator holder receiving the biological sterilization indicator; and
an infrared detector coupled to conditionally receive infrared radiation based on whether a biological sterilization indicator is in the biological sterilization indicator holder.

27. The apparatus of claim 26 wherein each biological sterilization indicator holder includes an inner surface formed of a material which reflects at least a portion of the fluorescence emitted by the biological sterilization indicator contained in the biological sterilization indicator holder.

28. The apparatus of claim 27 wherein the heater comprises:
a first heater; and
a second heater; and
wherein the plurality of biological sterilization indicator holders comprise a first plurality of biological sterilization indicator holders mounted operably proximate the first heater to receive heat from the first heater, and a second plurality of biological sterilization indicator holders mounted operably proximate the second heater to receive heat from the second heater.

29. A method of determining the adequacy of at least one sterilization cycle comprising the steps of:
a) providing an apparatus capable of reading a plurality of biological sterilization indicators, each biological sterilization indicator capable of exhibiting fluorescence to indicate a non-lethal sterilization cycle, the apparatus comprising:
plurality of biological sterilization indicator holders each sized, shaped and configured to receive one of the biological sterilization indicators;
a carriage controllably movable relative to thle plurality of biological sterilization indicator holders to positions proximate each of the biological sterilization indicator holders;
a radiation emitter mounted on the carriage and positioned to impinge radiation on a biological sterilization indicator received in a selected biological sterilization indicator holder when the carriage is in the position proximate the selected biological sterilization indicator holder;
a fluorescence sensor mounted on the carriage and positioned to sense fluorescence exhibited by the biological sterilization indicator in the selected biological sterilization indicator holder in response to the radiation impinged thereon and to provide a fluorescence signal indicative of the sensed fluorescence; and a controller coupled to the fluorescence sensor to receive the fluorescence signal and to provide an output signal indicative of the fluorescence sensed, the controller being configured to control the position of the carriage to intermittently position the carriage proximate each of the biological sterilization indicator holders then holding a biological steylization indicator and to receive the fluorescence signal indicative of the fluorescence sensed from the biological sterilization indicator corresponding to the biological sterilization indicator holder proximate which the carriage is then positioned;

b) providing a biological indicator capable of exhibiting fluorescence to indicate a non-lethal sterilization cycle;

c) Subjecting the biological indicator to a sterilization cycle;

d) then, placing the biological indicator in one of the biological sterilization indicator holders of the apparatus; and e) then determining the adequacy of a sterilization cycle with the apparatus.

30. A method of determining the adequacy of at least one sterilization cycle comprising the steps of:

a) providing an apparatus capable of reading a plurality of biological sterilization indicators to determine the efficacy of the one or more sterilization cycles, the biological sterilization indicators capable of exhibiting fluorescence to indicate a non-lethal sterilization cycle, the apparatus comprising:

a plurality of holders, each holder sized, shaped and configured to receive one of the plurality of biological sterilization indicators, each holder including a passage exposing a portion of the biological sterilization indicator received therein;

a heater coupled to the plurality of holders to heat the plurality of holders to at least one preselected temperature;

a carriage moveable relative to the plurality of holders among positions proximate each of the plurality of holders;

a radiation source, mounted on the carriage for movement with the carriage and configured to be operably aligned with the passage in a selected holder of the plurality of holders, when the carriage is in a position proximate the selected holder, to emit radiation through the passage in the selected holder;

a fluorescence sensor mounted on the carriage for movement with the carriage and configured to sense fluorescence exhibited by the biological sterilization. indicator in the selected holder, through the passage in the selected holder, and to provide a sensor signal indicative of the sensed fluorescence; and a first controller, mounted to the carriage for movement with the carriage and coupled to the fluorescence sensor and the radiation source, the first controller being configured to receive the sensor signal and provide a fluorescence signal based on the sensor signal;

b) providing a biological indicator capable of exhibiting fluorescence to indicate a non-lethal sterilization cycle;

c) subjecting the biological indicator to a sterilization cycle;

d) then placing the biological indicator in one of the biological sterilization indicator holders of the apparatus; and e) then determining the adequacy of the sterilization cycle with the apparatus.

* * * * *

UNITED STATES PATENT AND TRADEMARK OFFICE
CERTIFICATE OF CORRECTION

PATENT NO. : 6,025,189
DATED : February 15, 2000
INVENTOR(S) : Phillip A. Bolea and Thomas T. Rosenlund It is certified that error appears in the above-identified patent and that said Letters Patent is hereby corrected as shown below:

Column 2,
Line 21, delete "tryptic" and insert in place thereof -- cryptic --.

Column 4,
Line 27, delete "DI" and insert in place thereof -- BI --.

Column 16,
Line 16, delete "sterinization" and insert in place thereof -- sterilization --.

Column 17,
Line 8, delete "he" and insert in place thereof -- the --.
Line 15, delete "sterilzation" and insert in place thereof -- sterilization --.

Column 20,
Line 51, delete "thle" and insert in place thereof -- the --.

Signed and Sealed this

Seventh Day of May, 2002

*Attest:*

*Attesting Officer*

JAMES E. ROGAN
*Director of the United States Patent and Trademark Office*